US007229997B2

(12) United States Patent
Nilsson et al.

(10) Patent No.: US 7,229,997 B2
(45) Date of Patent: Jun. 12, 2007

(54) COMPOUNDS AND THEIR USE

(75) Inventors: Björn M. Nilsson, Stockholm (SE); Erik Ringberg, Uppsala (SE)

(73) Assignee: Biovitrum AB (SE)

(*) Notice: Subject to any disclaimer, the term of this patent is extended or adjusted under 35 U.S.C. 154(b) by 231 days.

(21) Appl. No.: 10/440,011

(22) Filed: May 16, 2003

(65) Prior Publication Data

US 2003/0232814 A1 Dec. 18, 2003

Related U.S. Application Data

(60) Provisional application No. 60/410,038, filed on Sep. 12, 2002.

(30) Foreign Application Priority Data

May 17, 2002 (SE) .................................... 0201544

(51) Int. Cl.
*A61K 31/497* (2006.01)
(52) U.S. Cl. .......................... 514/253.06; 514/253.01; 514/253.11; 544/360; 544/363; 544/364
(58) Field of Classification Search ................ 544/360, 544/363, 364; 514/253.01, 253.06, 253.11
See application file for complete search history.

(56) References Cited

U.S. PATENT DOCUMENTS 4,078,063 A 3/1978 Lumma, Jr. et al.
6,498,184 B2 * 12/2002 Berendsen .................. 514/428

FOREIGN PATENT DOCUMENTS

| EP | 0 370 560 A1 | 5/1990 |
| EP | 0 580 465 A1 | 1/1994 |
| EP | 1 213 017 A2 | 6/2002 |
| WO | WO 94/03430 | 2/1994 |
| WO | WO 98/33504 | 8/1998 |
| WO | WO 01/41701 A2 | 6/2001 |
| WO | WO 01/41701 A3 | 6/2001 |

OTHER PUBLICATIONS

Gaster et al. Annual Reports in Medicinal Chemistry, vol. 33, p. 21-30 (1998).*
Isaac et al. Bioorganic & Medicinal Chemistry letters, vol. 10, pp. 919-921 (2000).*
Nitsch et al. J. Biol. Chem. vol. 271, p. 4188-4194 (1996).*
Francois Jenck et al., "Antiaversive effects of 5HT$_{2C}$ receptor agonists and fluoxetine in a model of panic-like anxiety in rats", *European Neuropsychopharmacology*, vol. 8, Issue 3, pp. 161-168 (Aug. 1, 1998).
R.H.P. Porter et al., "Functional characterization of agonists at recombinant human 5-HT$_{2A}$, 5-HT$_{2B}$ and 5-HT$_{2C}$ receptors in CHO-K1 cells", *British Journal of Pharmacology*, vol. 128, pp. 13-20 (1999).
Andersson, "Pharmacology of penile erection." *Pharmacol. Rev.*, 53:417-450 (2001).
Andersson, "Treatment of the overactive bladder: possible central nervous system drug targets.", *Urology*, 59(Suppl 5A):18-24 (2002).
Applegate et al., "Global increases in seizure susceptibility in mice lacking 5-HT2C receptors: A behavioural analysis.", *Exp. Neurol.*, 154:522-530 (1998).
Arjona et al., "Effect of a 5-HT(2C) serotonin agonist, dexnorfenfluramine, on amyloid precursor protein metabolism in guinea pigs.", *Brain Res.*, 951:135-140 (2002).
Berendsen, "The role of serotonin in hot flushes", *Maturitas*, 36:155-164 (2000).
Bishop et al., "New 5-HT$_{2C}$ receptor agonists", *Expert Opin. Ther. Patents*, 13(11):1691-1705 (2003).
Chojnacka-Wojcik et al., "Involvement of 5-HT2C receptors in the m-CPP-induced antinociception in mice." *Pol J Pharmacol.*, 46(5):423-428 (1994).
Cryan et al., "Antidepressant-like behavioral effects mediated by 5-Hydroxytryptamine(2C) receptors." *J. Pharmacol Exp. Ther.*, 295(3):1120-1126 (2000).
de Groat et al., "Influence of central serotoneric mechanisms on lower urinary tract function." *Urology*, 59(Suppl. 5A):30-36 (2002).
Dhonnchadha, et al., "Anxiolytic-like effects of 5-HT2 ligands on three mouse models of anxiety", *Behavioural Brain Research*, 140(1-2):203-214 (2003).
Goodman and Gilman's, The Pharmalogical basis of Therapeutics, 8$^{th}$ ed., McGraw-Hill, Int. Ed. 1992, "Biotransformation of Drugs", p. 13-15.
Grottick et al., "Activation of 5-HT(2C) receptors reduces the locomotor and rewarding effects of nicotine." *Psychopharmacology (Berl)*, 157(3):292-8 (2001).
Grottick et al., "Studies to investigate the role of 5-HT(2C) receptors on cocaine- and food-maintained behavior." *J Pharmacol Exp Ther.*, 295(3):1183-91 (2000).

(Continued)

Primary Examiner—James O. Wilson
Assistant Examiner—Ebenezer Sackey
(74) Attorney, Agent, or Firm—Fish & Richardson P.C.

(57) ABSTRACT

Compounds of the general formula (I):

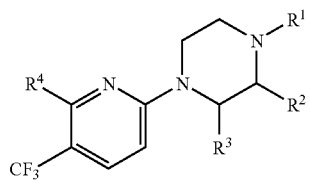

wherein $R^1$, $R^2$, $R^3$ and $R^4$ are as described in the specification.

Further included are pharmaceutical compositions comprising the compounds, processes for their preparation, as well as the use of the compounds for the preparation of a medicament which particularly acts on the central nervous system, particularly for use as anti-obesity agents.

19 Claims, No Drawings

OTHER PUBLICATIONS

Guarneri et al., "The effects of m-CPP on bladder voiding contractions in rats are mediated by the 5-HT2A/5-HT2C receptors.", *Neurourol. Urodyn.*, 15:316-317 (1996).

Heisler et al., "Epilepsy and obesity in serotonin 5-HT2C receptor mutant mice." *Ann NY Acad Sci*, 861:74-78 (1998).

Isaac, "The 5-HT2C receptor as a potential therapeutic target for the design of antiobesity and antiepileptic drugs.", *Drugs Future*, 26:383-393 (2001).

Kenakin, "Inverse, protean, and ligand-selective agonism: matters of receptor conformation," *The FASEB Journal*, 15:598-611 (2001).

Millan et al., "5-HT2C receptors mediate penile erections in rats: actions of novel and selective agonists and antagonists.", *Eur. J. Pharamcol.*, 325:9-12 (1997).

Moreau et al., "5HT2C receptor agonists exhibit antidepressant-like properties in the anhedonia model of depression in rats." Pharma Division, Preclinical CNS Research, F. Hoffmann-La Roche Ltd, Basel, Switz. European Neuropyschopharmacology (1996), 6(3):169-175. Coden:Eurne8 Issn: 0924-977X. Journal written in English. CAN 125:265667 AN 1996:491063 CAPLUS.

Nonogaki et al., "Leptin-independent hyperphagia and type 2 diabetes in mice with a mutated serotonin 5-HT$_{2C}$ receptor gene", *Nature Medicine*, 4(10):1152-1156 (1998).

Piesla et al., "Atypical antipsychotic-like effects of 5-HT2C agonists." *Schizophrenia Res.*, 49(1-2):95-95 Sp. Iss. SI Suppl. S, Apr. 15, 2001.

Pornerantz, "5-HTIA and 5-HTIC/D receptor agonists produce reciprocal effects on male sexual behavior of rhesus monkeys.", *Eur. J. Pharmacol.*, 243:227-234 (1993).

Porter, et al., "Functional characterization of agonists at recombinant human 5-HT$_{2A}$, 5-HT$_{2B}$ and 5-HT$_{2C}$ receptors in CHO-K1 cells", *British Journal of Pharmacology*, 128:13-20 (1999).

Pranzatelli et al., "Identification of spinal 5-HT1C binding sites in the rat: characterization of [3H]mesulergine binding." *J. Pharmacol. Exp. Ther.*, 261:161-165 (1992).

Steers et al., "Effects of m-chlorophenylpiperazine on penile and bladder function in rats.", *Am. J. Physiol.*, 257:R1441-R1449 (1989).

Steers et al., "Effects of serotonergic agonists on micturition and sexual function in the rat." *Drug Dev. Res.*, 27:361-375 (1992).

Szele et al., "Effects of fenfluramine, m-chlorophenylpiperazine, and other serotonin-related agonists and antagonists on penile erections in nonhuman primates.", *Life Sci.*, 43:1297-1303 (1998).

Tecott et al., "Eating disorder and epilepsy in mice lacking 5-HT2C serotonin receptors." *Nature*, 374:542-546 (1995).

Testa et al., "Effect of different 5-hydroxytryptamine receptor subtype antagonists on the micturition reflex in rats.", *BJU Int.*, 87:256-264 (2001).

Upton et al., "Studies on the role of 5-HT2C and 5-HT2B receptors in regulating generalized seizure threshold in rodents." *Eur. J. Pharmacol.*, 359:33-40 (1998).

* cited by examiner

COMPOUNDS AND THEIR USE

RELATED APPLICATIONS

This application claims priority to Swedish application number 0201544-4, filed on May 17, 2002, and U.S. provisional application 60/410,038, filed on Sep. 12, 2002, the contents of which are incorporated herein by reference.

TECHNICAL FIELD

The present invention relates to novel compounds, to pharmaceutical compositions comprising the compounds, to processes for their preparation, as well as to the use of the compounds for the preparation of a medicament which particularly acts on the central nervous system.

BACKGROUND ART

Many disorders and conditions of the central nervous system are influenced by the adrenergic, the dopaminergic, and the serotonergic neurotransmitter systems. For example, serotonin (5-HT; 5-hydroxytryptamine) has been implicated in a number of disorders and conditions which originate in the central nervous system. A number of pharmacological and genetic experiments involving receptors for serotonin strongly implicate the $5\text{-HT}_{2c}$ receptor subtype in the regulation of food intake, see for example Obes. Res. 1995, 3, Suppl. 4, 449S–462S and Drugs Future 2001, 26, 383–393. The $5\text{-HT}_{2c}$ receptor subtype is transcribed and expressed in hypothalamic structures associated with appetite regulation. It has been demonstrated that the $5\text{-HT}_{2c}$ receptor agonist m-chlorophenylpiperazine (mCPP), which has some preference for the $5\text{-HT}_{2c}$ receptor, reduces food intake in mice that express the normal $5\text{-HT}_{2c}$ receptor while the compound lacks activity in mice expressing the mutated inactive form of the $5\text{-HT}_{2c}$ receptor (Nature 1995, 374, 542–546). In a recent clinical study, a slight but sustained reduction in body weight was obtained after 2 weeks of treatment with mCPP in obese subjects (Psychopharmacology 1997, 133, 309–312). Recently, a series of pyrrolo[3,2,1-ij]quinoline derivatives was identified to be $5\text{-HT}_{2c}$ receptor agonists having selectivity over the $5\text{-HT}_{2a}$ receptor (Isaac M., et al., Bioorg. Med. Chem. Lett. 2000, 10, 919–921). The compounds are said to offer a novel approach to the treatment of obesity and epilepsy.

Weight reduction has also been reported from clinical studies with other "serotonergic" agents (see e.g. IDrugs 1998, 1, 456–470). For example, the 5-HT reuptake inhibitor fluoxetine and the 5-HT releasing agent/reuptake inhibitor dexfenfluramine have exhibited weight reduction in controlled studies. However, currently available drugs that increase serotonergic transmission appear to have only a moderate and, in some cases, transient effects on the body weight.

The $5\text{-HT}_{2c}$ receptor subtype has also been suggested to be involved in CNS disorders such as depression and anxiety (Exp. Opin. Invest. Drugs 1998, 7, 1587–1599; IDrugs, 1999, 2, 109–120).

The $5\text{-HT}_{2c}$ receptor subtype has further been suggested to be involved in urinary disorders such as urinary incontinence (IDrugs, 1999, 2, 109–120).

Compounds which have an effect on the $5\text{-HT}_{2c}$ receptor may therefore have a therapeutic potential in the treatment of disorders like those mentioned above.

INFORMATION DISCLOSURE

U.S. Pat. No. 3,253,989 discloses the use of mCPP as an anorectic agent.

EP-A1-863 136 discloses azetidine and pyrrolidine derivatives which are selective $5\text{-HT}_{2c}$ receptor agonists having antidepressant activity and which can be used for treating or preventing serotonin-related diseases, including eating disorders and anxiety.

EP-A-657 426 discloses tricyclic pyrrole derivatives having activity on the $5\text{-HT}_{2c}$ receptor and which inter alia may be used for treating eating disorders.

EP-A-655 440 discloses 1-aminoethylindoles having activity on the $5\text{-HT}_{2c}$ receptor and which may be used for treating eating disorders.

EP-A-572 863 discloses pyrazinoindoles having activity on the $5\text{-HT}_{2c}$ receptor and which may be used for treating eating disorders.

J. Med. Chem. 1978, 21, 536–542 and U.S. Pat. No. 4,081,542 disclose a series of piperazinylpyrazines having central serotonin-mimetic activity.

U.S. Pat. No. 4,078,063 discloses a series of piperazinylpyridines having anorexic activity.

J. Med. Chem. 1981, 24, 93–101 discloses a series of piperazinylquinoxalines with central serotoninmimetic activity.

ES 514549 discloses piperazine derivative with anorexigenic action.

EP 370560 discloses 1-[mono- or bis(trifluoromethyl)-2-pyridinyl]piperazines as central nervous system agents.

WO 98/33504 discloses a new medical use of 1-[6-chloro-5-(trifluoromethyl)-2-pyridinyl]piperazine, in particular to a new method of treating urinary incontinence.

WO 02/30902 discloses crystal forms of 1-[6-chloro-5-(trifluoromethyl)-2-pyridinyl]piperazine hydrochloride.

EP 1213017 discloses the use of a $5\text{-HT}_{2c}$ receptor agonist, e.g., 1-[6-chloro-5-(trifluoromethyl)-2-pyridinyl]piperazine, for the treatment of hot flushes.

J. Med Chem. 1987, 30, 1210–1214 discloses N,N-disubstituted 6-alkoxy-2-pyridinamines as anticonvulsant agents including 1-(6-methoxy-2-pyridinyl)piperazine, 1-(6-ethoxy-2-pyridinyl)piperazine, 1-(6-isopropoxy-2-pyridinyl)piperazine, 1-(6-isobutoxy-2-pyridinyl)piperazine, 1-(6-cyclopropylmethoxy-2-pyridinyl)piperazine, 1-(6-cyclohexylmethoxy-2-pyridinyl)piperazine, and 1-(6-cyclohexyloxy-2-pyridinyl)piperazine.

J. Med. Chem. 1989, 32, 1237–1242 discloses 6-alkyl-N,N-disubstituted-2-pyridinamines as anticonvulsant agents including 1-(6-butylthio-2-pyridinyl)piperazine, 1-(6-cyclohexylmethyl-2-pyridinyl)piperazine and 1-[6-(2-phenylethyl)-2-pyridinyl]piperazine.

JP 07300474 discloses drugs for treatment of diseases related to serotoninergic nerve including 1-(6-phenoxy-2-pyridinyl)piperazine and 1-[6-(substituted)phenoxy-2-pyridinyl]piperazines, 1-(6-benzyloxy-2-pyridinyl)piperazine, 1-(6-cyclobutyloxy-2-pyridinyl)piperazine, and 1-(6-cyclopentyloxy-2-pyridinyl)piperazine EP 580465 discloses heterocyclic piperazines as $5\text{-HT}_3$ agonists including 6-chloro-2-(3-methylpiperazinyl)pyridine and 6-chloro-2-(4-methylpiperazinyl)pyridine.

WO 00/12475 discloses indoline derivatives as $5\text{-HT}_{2b}$ and/or $5\text{-HT}_{2c}$ receptor ligands, especially for the treatment of obesity.

WO 00/12510 discloses pyrroloindoles, pyridoindoles and azepinoindoles as $5\text{-HT}_{2c}$ receptor agonists, particularly for the treatment of obesity.

WO 00/12482 discloses indazole derivatives as selective, directly active 5-HT$_{2c}$ receptor ligands, preferably 5-HT$_{2c}$ receptor agonists, particularly for use as anti-obesity agents.

WO 00/12502 discloses pyrroloquinolines as 5-HT$_{2c}$ receptor agonists, particularly for use as anti-obesity agents.

WO 00/35922 discloses 2,3,4,4a-tetrahydro-1H-pyrazino[1,2-a]quinoxalin-5(6H)ones as 5HT$_{2c}$ agonists, which may be used for the treatment of obesity.

WO 00/44737 discloses aminoalkylbenzofurans as 5-HT$_{2c}$ agonists, which may be used for the treatment of obesity.

Further compounds reported to be 5HT$_{2c}$ receptor agonists are, for example, indazolylpropylamines of the type described in WO 00/12481; indazoles of the type described in WO 00/17170; piperazinylpyrazines of the type described in WO 00/76984; WO 02/40456 and WO 02/40457; heterocycle fused γ-carbolines of the type described in WO 00/77001, WO 00/77002 and WO 00/77010; benzofurylpiperazines of the type described in WO 01/09111 and WO 01/09123; benzofurans of the type described in WO 01/09122; benzothiophenes of the type described in 01/09126; aminoalkylindazoles of the type described in WO 98/30548; indoles of the type described in WO 01/12603; indolines of the type described in WO 01/12602 and WO 02/44152; pyrazino(aza)indoles of the type described in WO 00/44753; diaza-cyclopenta[a]indenes of the type described in EP 1132389; piperazine derivatives of the type described in WO 02/10169; WO 02/72584 and WO 02/48124; quinoxalinones of the type described in U.S. Pat. No. 6,372,745, and tricyclic pyrroles or pyrazoles of the type described in WO 98/56768.

WO 95/01976 discloses indoline derivatives active as 5-HT$_{2c}$ antagonists and of potential use in the treatment of CNS disorders.

WO 99/58490 discloses aryl-hydronaphthalen-alkanamines which may effectuate partial or complete blockage of serotonergic 5-HT$_{2c}$ receptors in an organism.

WO 03/00666 discloses [1,2']bipyrazinyl 5-HT$_2$ receptor ligands, in particular 5-HT$_{2c}$ receptor ligands, for the treatment of sexual dysfunction.

WO 03/00663 discloses piperazinylpyrimidines as 5-HT$_2$ receptor ligands, in particular 5-HT$_{2c}$ receptor ligands, for the treatment of sexual disorders.

WO 02/51844 discloses cycloalkyl fused indole derivatives and their use as 5-HT$_{2b}$ and 5-HT$_{2c}$ receptor ligands.

WO 02/42304 discloses cyclopenta[b][1,4]diazepino[6,7-hi]indoles as selective 5-HT$_{2c}$ receptor agonists.

WO 02/36596 discloses diazepinocarbazoles and related compounds as serotonin 5-HT$_{2c}$ agonists.

SUMMARY OF THE INVENTION

According to the invention novel compounds of the general formula (I) are provided:

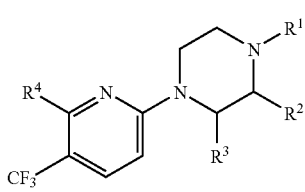

(I)

wherein
$R^1$ is selected from H, $C_{1-4}$ alkyl, 2-hydroxyethyl, 2-cyanoethyl, tetrahydropyran-2-yl, and a nitrogen protecting group;
$R^2$ and $R^3$ each, independently, represent H or $CH_3$;
$R^4$ is selected from halogen, O—$R^5$, NH—$R^5$ or S—$R^5$, wherein
$R^5$ is selected from aryl, aryl-$C_{1-6}$-alkyl, aryloxy-$C_{2-6}$-alkyl, heteroaryl, heteroaryl-$C_{1-6}$-alkyl, heteroaryloxy-$C_{2-6}$-alkyl, $C_{3-6}$-cycloalkyl, $C_{3-6}$-cycloalkyl-$C_{1-4}$-alkyl, $C_{1-6}$-alkyl, 2-tetrahydrofuryl, 3-tetrahydrofuryl, 2-tetrahydrofurfuryl, 3-tetrahydrofurfuryl, piperidine-4-yl, tetrahydropyran-4-yl, $C_{3-6}$-alkynyl, $C_{3-6}$-alkenyl, or fluoro-$C_{2-4}$-alkyl;

and wherein any aryl or heteroaryl residue, alone or as part of another group, may be unsubstituted or substituted with one or more of $C_{1-4}$-alkyl, $C_{1-4}$-alkoxy, $C_{1-4}$-alkylthio, $C_{2-4}$-acyl, $C_{1-4}$-alkylsulphonyl, cyano, nitro, hydroxy, $C_{2-6}$-alkenyl, $C_{2-6}$-alkynyl, fluoromethyl, trifluoromethyl, trifluoromethoxy, halogen, —N($R^6$)($R^7$), aryl, aryloxy, arylthio, aryl-$C_{1-4}$-alkyl, aryl-$C_{2-4}$-alkenyl, aryl-$C_{2-4}$-alkynyl, heteroaryl, heteroaryloxy, heteroarylthio, heteroaryl-$C_{1-4}$-alkyl, aryl-$C_{1-4}$-alkoxy, aryloxy-$C_{1-4}$-alkyl, or dimethylamino-$C_{2-4}$-alkoxy, wherein
$R^6$ and $R^7$ are, independently of each other, hydrogen, methyl or ethyl; or form a pyrrolidine, piperazine, morpholine, thiomorpholine or a piperidine ring together with the nitrogen atom to which they are bound;

and wherein any aryl or heteroaryl residue as substituents on aryl or heteroaryl, alone or as part of another group, in turn may be substituted in one or more positions, preferably one, independently of each other by $C_{1-4}$-alkyl, $C_{1-4}$-alkoxy, halogen, trifluoromethyl, cyano, hydroxy or dimethylamino;

and pharmaceutically acceptable salts, hydrates, solvates, geometrical isomers, tautomers, optical isomers, N-oxides and prodrug forms thereof, with the proviso that, when $R^4$ is halogen at least one of $R^1$, $R^2$, or $R^3$ is not hydrogen.

When $R^4$ is halogen, it is preferred that either:
(i) $R^1$ is selected from $C_{1-4}$ alkyl, 2-hydroxyethyl, 2-cyanoethyl, tetrahydropyran-2-yl, and a nitrogen protecting group; or
(ii) $R^1$ is selected from H, $C_{1-4}$ alkyl, 2-hydroxyethyl, 2-cyanoethyl, tetrahydropyran-2-yl, and a nitrogen protecting group; and at least one of $R^2$ and $R^3$ is $CH_3$;

In case the compounds of formula (I) can be in the form of optical isomers, the invention comprises the racemic mixture as well as the individual enantiomers as such.

In case the compounds of formula (I) contain groups, which may exist in tautomeric forms, the invention comprises the tautomeric forms of the compounds as well as mixtures thereof.

In case the compounds of formula (I) can be in the form of geometrical isomers, the invention comprises the geometrical isomers as well as mixtures thereof.

According to another aspect, the invention provides the compounds according to formula (I) above for use in therapy.

Still another aspect of the invention provides a pharmaceutical composition comprising a compound according to formula (I) above as the active ingredient, preferably together with a pharmaceutically acceptable carrier and, if desired, other pharmacologically active agents.

In yet another aspect, the invention provides a method for the treatment of a human or animal subject suffering from a serotonin-related disorder or condition, particularly 5-HT$_{2c}$ receptor-related, such as memory disorders including Alzheimer's disease; schizophrenia; mood disorders; anxiety disorders; pain; substance abuse; sexual dysfunction; epilepsy; glaucoma; urinary incontinence; menopausal and post-menopausal hot flushes; type II diabetes; eating disorders, such as binge eating disorders, anorexia nervosa and bulimia; and weight gain associated with antipsychotic drug administration; and particularly obesity. The method includes administering an effective amount of a compound of formula (I), or a composition having a compound of formula (I) in it.

Another aspect of the invention relates to the use of the compounds of formula (I) for the manufacture of a medicament for the treatment of a serotonin-related disorder or condition, particularly $5\text{-HT}_{2c}$ receptor-related, such as memory disorders including Alzheimer's disease; schizophrenia; mood disorders; anxiety disorders; pain; substance abuse; sexual dysfunction; epilepsy; glaucoma; urinary incontinence; menopausal and post-menopausal hot flushes; type II diabetes; eating disorders, such as binge eating disorders, anorexia nervosa and bulimia; and weight gain associated with antipsychotic drug administration; and particularly obesity. In one aspect, the manufacture of a medicament for the treatment of a serotonin-related disorder or condition can include the step of preparing a pharmaceutical composition having a compound of any of the formulae described herein and a pharmaceutically acceptable carrier. A method for preparing the pharmaceutical composition can include the step of combining a compound of any of the formulae described herein and a pharmaceutically acceptable carrier.

Finally a method for modulating $5\text{HT}_{2c}$ receptor function is an aspect of the invention.

The methods delineated herein can also include the step of identifying that a subject is in need of treatment of serotonin-related disorders or conditions, particularly $5\text{-HT}_{2c}$ receptor-related, in the subject.

DETAILED DESCRIPTION OF THE INVENTION

According to the present invention, a class of novel compounds that bind to the $5\text{-HT}_{2c}$ receptor has been developed. The compounds may act as receptor agonists or antagonists at the $5\text{-HT}_{2c}$ receptor and may therefore be used for the treatment of serotonin-related disorders or conditions, particularly $5\text{-HT}_{2c}$ receptor-related.

First, the various terms used, separately and in combinations, in the above definition of the compounds having the general formula (I) will be explained.

The expression "$C_{1-6}$ alkyl" refers to straight-chained and branched alkyl groups containing from 1 to 6 carbon atoms. Particular $C_{1-6}$ alkyl groups are methyl, ethyl, n-propyl, isopropyl, tert-butyl, n-pentyl, isopentyl, n-hexyl, and isohexyl. Derived expressions such as "$C_{1-4}$ alkoxy" and "$C_{1-4}$ alkylthio" are to be constructed accordingly.

The expression "$C_{2-6}$ alkenyl" as used herein refers to straight-chained and branched alkenyl groups containing from 2 to 6 carbon atoms. Typical examples include vinyl, allyl, 3,3-dimethylallyl, 1-butenyl, and 2-butenyl groups.

The expression "$C_{2-6}$ alkynyl" as used herein refers to straight-chained and branched alkynyl groups containing from 2 to 6 carbon atoms. Typical examples include ethynyl and propargyl groups.

By "heteroatom" is meant nitrogen, oxygen, sulphur, and in heterocyclic rings (including heteroaromatic as well as saturated and partially saturated heterocyclic rings), also selenium.

The term "aryl" is intended to include aromatic rings (monocyclic or bicyclic) having from 6 to 10 ring carbon atoms, such as phenyl, 1-naphthyl, 2-naphthyl, 1,2,3,4-tetrahydronaphthyl, and indanyl. The aryl group can be linked to the remainder of the molecule via a carbon atom in any ring.

The term "heteroaryl" means a mono- or bicyclic aromatic ring system, only one ring need be aromatic, and which can be linked to the remainder of the molecule via a carbon or nitrogen atom in any ring, and having from 5 to 10 ring atoms (mono- or bicyclic), in which one or more of the ring atoms are heteroatoms such as nitrogen, sulphur, oxygen and selenium and the remainder are carbon atoms. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, coumarin, quinoline, quinoxaline, isoquinoline, phthalazine, cinnoline, quinazoline, indole, isoindole, indoline, isoindoline, benzothiophene, benzofuran, 2,3-dihydrobenzofuran, isobenzofuran, benzoxazole, 2,1,3-benzoxadiazole, benzothiazole, 2,1,3-benzothiadiazole, 2,1,3-benzoselenadiazole, benzimidazole, indazole, 2,3-dihydro-1,4-benzodioxine, 1,3-benzodioxole, 1,2,3,4-tetrahydroquinoline, 3,4-dihydro-2H-1,4-benzoxazine, 1,5-naphthyridine, 1,8-naphthyridine, 3,4-dihydro-2H-pyrido[3,2-b]-1,4-oxazine, and 2,3-dihydro-1,4-benzoxathiine. If a bicyclic aryl or heteroaryl ring is substituted, it may be substituted in any ring.

Exemplary aryl-$C_{1-6}$-alkyl, in which the alkyl portion of the group may be straight or branched, include benzyl, 2-naphthylmethyl, 2-phenylethyl, 3-phenyl-1-propyl, 1-phenylethyl, 1-phenyl-2-propyl, 2-phenyl-1-propyl and the like.

Exemplary aryloxy-$C_{2-6}$-alkyl, in which the alkyl portion of the group may be straight or branched, include 2-phenoxyethyl, 2-(1-naphthyloxy)ethyl, 3-(2-naphthyloxy)-1-propyl, 3-phenoxy-1-propyl, 4-phenoxy-1-butyl, 5-phenoxy-1-pentyl, 1-phenoxy-2-propyl and the like.

Exemplary $C_{3-6}$-cycloalkyl-$C_{1-4}$-alkyl, in which the alkyl portion of the group may be straight or branched, include cyclopropylmethyl, cyclopentylmethyl, 2-cyclohexylethyl, 1-cyclohexylethyl, 1-cyclopropylethyl, 1-cyclobutylethyl and the like.

Exemplary heteroaryloxy-$C_{2-6}$-alkyl include 2-(8-quinolinyloxy)ethyl, 2-(3-pyridinyloxy)ethyl, 3-(8-quinolinyloxy)propyl and the like.

Halogen includes fluorine, chlorine, bromine or iodine, preferably fluorine, chlorine or bromine.

Where it is stated above that aryl and heteroaryl residues may be substituted (in one or more positions), this applies to aryl and heteroaryl per se as well as to any combined groups containing aryl or heteroaryl residues, such as heteroaryloxy-$C_{2-6}$-alkyl, aryl-$C_{1-6}$-alkyl etc.

The term "N-oxides" means that one or more nitrogen atoms, when present in a compound, are in N-oxide form ($N{\rightarrow}O$).

The term "prodrug forms" means a pharmacologically acceptable derivative, such as a carbamate or an amide, which derivative is biotransformed in the body to form the active drug. Reference is made to Goodman and Gilman's, The Pharmacological basis of Therapeutics, 8th ed., McGraw-Hill, Int. Ed. 1992, "Biotransformation of Drugs", p. 13–15.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, malic acid, oxalic acid, toluenesulphonic acid, methanesulphonic acid, fumaric acid, succinic acid, tartaric acid, citric acid, benzoic acid, ascorbic acid and the like.

The expression "comprising" means "including but not limited to." Thus, other non-mentioned substances, additives or carriers may be present.

"A nitrogen protecting group" (i e a value for $R^1$) refers to a group covalently bonded to a nitrogen atom, or any group used to derivatize nitrogen atom (e.g., the nitrogen atom in an amino group). The group may be introduced or cleaved off by conventional methods such as those described in Protective Groups in Organic Synthesis, John Wiley & Sons, 1991. Examples of the nitrogen protecting groups include trityl or t-butoxycarbonyl and those delineated in Protective Groups in Organic Synthesis, John Wiley & Sons, 1991 and subsequent editions thereof.

It is preferred that $R^1$ is hydrogen.

It is also preferred that $R^4$ is selected from chlorine, O—$R^5$, and S—$R^5$.

It is also preferred that $R^5$ is selected from aryl-$C_{1-6}$-alkyl, aryloxy-$C_{2-6}$-alkyl, heteroaryl-$C_{1-6}$-alkyl, heteroaryloxy-$C_{2-6}$-alkyl, $C_{3-6}$-cycloalkyl, $C_{3-6}$-cycloalkyl-$C_{1-4}$-alkyl, $C_{1-6}$-alkyl, 2-tetrahydrofurfuryl, and wherein any aryl or heteroaryl residue, alone or as part of another group, may be unsubstituted or substituted with one or more of $C_{1-4}$-alkyl, $C_{1-4}$-alkoxy, cyano, halogen, aryloxy-$C_{1-4}$-alkyl.

It is more preferred that $R^5$ is selected from benzyl, 2-chlorobenzyl, 3-cyanobenzyl, 2-cyclohexylethyl, cyclopentyl, 2-cyclopentylethyl, 2,3-difluorobenzyl, 2,6-difluorobenzyl, 2-(2,6-difluorophenoxy)ethyl, 2,3-dihydrobenzo[1,4]dioxin-6-ylmethyl, ethyl, 5-fluoro-2-methoxybenzyl, furan-2-ylmethyl, methyl, α-methylbenzyl, 3-methylbenzyl, 2-(naphthalene-2-yloxy)ethyl, 2-phenoxyethyl, 2-phenoxymethylbenzyl, n-propyl, 3-(pyridin-3-yl)-n-propyl, 2-(8-quinolinyloxy)ethyl, tetrahydrofuran-2-ylmethyl, 3-thienylmetyl.

It is also preferred that the carbon atom, to which $R^2$ is attached, is in the (S)-configuration when $R^2$ is methyl and $R^1$ and $R^3$ both are hydrogen.

It is also preferred that the carbon atom, to which $R^3$ is attached, is in the (R)-configuration when $R^3$ is methyl and $R^1$ and $R^2$ both are hydrogen.

Preferred compounds of the general formula (I) above are the following compounds (corresponding to Examples 6–43 below):

1-(6-Chloro-5-trifluoromethyl-pyridin-2-yl)-3-(S)-methyl-piperazine 1-(6-Chloro-5-trifluoromethyl-pyridin-2-yl)-3-(R)-methylpiperazine 1-(6-Chloro-5-trifluoromethyl-pyridin-2-yl)-2-(R)-methyl-piperazine 1-(6-Chloro-5-trifluoromethyl-pyridin-2-yl)-2-(S)-methyl-piperazine, hydrochloride 1-[6-(2-Phenoxy-ethoxy)-5-trifluoromethyl-pyridin-2-yl]-piperazine, acetate 1-[6-(2,3-Dihydro-benzo[1,4]dioxin-6-ylmethoxy)-5-trifluoromethyl-pyridin-2-yl]-piperazine, acetate 1-[6-(Thiophen-3-ylmethoxy)-5-trifluoromethyl-pyridin-2-yl]-piperazine, acetate 3-(6-Piperazin-1-yl-3-trifluoromethyl-pyridin-2-yloxymethyl)-benzonitrile, acetate 1-[6-(3-Methyl-benzylsulfanyl)-5-trifluoromethyl-pyridin-2-yl]-piperazine, acetate 1-[6-(2-Chloro-benzylsulfanyl)-5-trifluoromethyl-pyridin-2-yl]-piperazine, acetate 1-[6-(2,3-Difluoro-benzyloxy)-5-trifluoromethyl-pyridin-2-yl]-piperazine, acetate 1-(6-Ethylsulfanyl-5-trifluoromethyl-pyridin-2-yl)-piperazine, acetate 1-(6-Propoxy-5-trifluoromethyl-pyridin-2-yl)-piperazine, acetate 1-(6-Cyclopentyloxy-5-trifluoromethyl-pyrdin-2-yl)-piperazine, acetate 1-[6-(1-Phenyl-ethoxy)-5-trifluoromethyl-pyridin-2-yl]-piperazine, acetate 8-[2-(6-Piperazin-1-yl-3-trifluoromethyl-pyridin-2-yloxy)-ethoxy]-quinoline, acetate 1-[6-(2,6-Difluoro-benzyloxy)-5-trifluoromethyl-pyridin-2-yl]-piperazine, acetate 1-[6-(3-{Pyridin-3-yl}propoxy)-5-trifluoromethyl-pyridin-2-yl]-piperazine, acetate 1-(6-Benzyloxy-5-trifluoromethyl-pyrdin-2-yl)-piperazine, acetate 1-[6-(Furan-2-ylmethoxy)-5-trifluoromethyl-pyridin-2-yl]-piperazine, acetate 1-{6-[2-(2,6-Difluoro-phenoxy)-ethoxy]-5-trifluoromethyl-pyrdin-2-yl}-piperazine, acetate 1-[6-(2-Chloro-benzylsulfanyl)-5-trifluoromethyl-pyridin-2-yl]-2-(R)-methyl-piperazine, acetate 1-(6-Ethylsulfanyl-5-trifluoromethyl-pyridin-2-yl)-3-(S)-methyl-piperazine, acetate 1-(6-Ethylsulfanyl-5-trifluoromethyl-pyridin-2-yl)-3-(R)-methyl-piperazine, acetate 1-(6-Ethylsulfanyl-5-trifluoromethyl-pyridin-2-yl)-2-(R)-methyl-piperazine, acetate 1-(6-Benzyloxy-5-trifluoromethyl-pyridin-2-yl)-3-(S)-methyl-piperazine, acetate 1-(6-Benzyloxy-5-trifluoromethyl-pyridin-2-yl)-3-(R)-methyl-piperazine, acetate 1-(6-Benzyloxy-5-trifluoromethyl-pyridin-2-yl)-2-(R)-methyl-piperazine, acetate 1-(6-Benzyloxy-5-trifluoromethyl-pyridin-2-yl)-2-(S)-methyl-piperazine, acetate 1-(6-Methoxy-5-trifluoromethyl-pyridin-2-yl)-piperazine, acetate 1-[6-(5-Fluoro-2-methoxy-benzyloxy)-5-trifluoromethyl-pyridin-2-yl]-piperazine, acetate 1-{6-[2-(Naphthalen-2-yloxy)-ethoxy]-5-trifluoromethyl-pyridin-2-yl}-piperazine, acetate 1-[6-(2-Chloro-benzylsulfanyl)-5-trifluoromethyl-pyridin-2-yl]-3-(S)-methyl-piperazine, acetate 1-[6-(2-Chloro-benzylsulfanyl)-5-trifluoromethyl-pyridin-2-yl]-2-(S)-methyl-piperazine, acetate 1-[6-(2-Phenoxymethyl-benzyloxy)-5-trifluoromethyl-pyridin-2-yl]-piperazine, acetate 1-[6-Tetrahydro-furan-2-ylmethoxy)-5-trifluoromethyl-pyridin-2-yl]-piperazine, acetate 1-[6-(2-Cyclopentyl-ethoxy)-5-trifluoromethyl-pyridin-2-yl]-piperazine, acetate 1-[6-(2-Cyclohexyl-ethoxy)-5-trifluoromethyl-pyridin-2-yl]-piperazine, acetate and their pharmacologically acceptable salts and solvates.

The compounds corresponding to Examples 6, 8, 10–38, and 41–43 are even more preferred.

As mentioned above, the compounds of the present invention are useful for the treatment, including prophylactic treatment, of serotonin-related, especially 5-HT$_{2c}$ receptor-related, disorders and conditions, in a human being or in an animal, including e.g. pets, such as memory disorders including Alzheimer's disease; schizophrenia; mood disorders, including, but not restricted to, major depression and bipolar depression, including both mild and manic bipolar disorder, seasonal affective disorder (SAD); anxiety disorders, including situational anxiety, generalized anxiety disorder, primary anxiety disorders (panic disorders, phobias, obsessive-compulsive disorders, and post-traumatic stress disorders), and secondary anxiety disorders (for example anxiety associated with substance abuse); pain; substance abuse; sexual dysfunction; epilepsy; glaucoma; urinary incontinence; menopausal and post-menopausal hot flushes; type II diabetes; eating disorders, such as binge eating disorders, anorexia nervosa and bulimia; weight gain associated with antipsychotic drug administration; and particularly obesity.

The compounds of the present invention in radiolabelled form, may be used as a diagnostic agent.

Processes for Preparation

This invention also relates to methods of making compounds of any formulae delineated herein comprising reacting any one or more of the compounds or formulae delineated herein including any processes delineated herein.

In one aspect, the invention is a method of making a compound of formula (I) delineated herein. The compounds of general formula (I) above may be prepared by, or in analogy with, conventional methods, and especially according to or in analogy with the following method.

Compounds of formula (I) above in which R$^4$ is halogen, O—R$^5$, NH—R$^5$ or S—R$^5$ are prepared by reacting a compound of the structural formula (II):

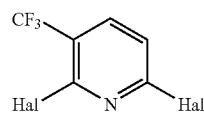

(II)

wherein Hal is halogen; with 1 to 10 molar equivalents of an appropriate piperazine derivative of formula (III):

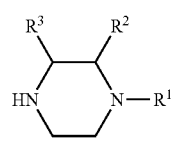

(III)

wherein R$^1$, R$^2$, and R$^3$ are as defined above; in a solvent such as dimethylsulfoxide (DMSO), acetonitrile, dioxane, tetrahydrofuran (THF), n-butanol, N,N-dimethylformamide (DMF), or in a mixture of solvents such as DMF/dioxane, optionally in the presence of a base, such as K$_2$CO$_3$, Na$_2$CO$_3$, Cs$_2$CO$_3$, NaOH, triethylamine, pyridine or the like, at 0–200° C. for 1–24 hours to produce a compound of formula (IV):

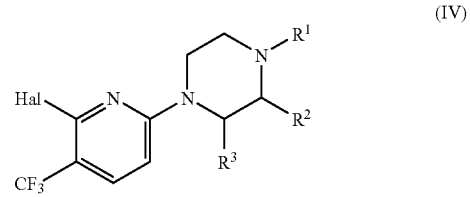

(IV)

wherein R$^1$, R$^2$, and R$^3$ are as defined above and Hal is halogen.

The compound of formula (IV) is reacted with an appropriate alcohol, amine, or thiol as defined by O—R$^5$, NH—R$^5$ or S—R$^5$ above, or its corresponding anions to produce a compound of the formula (I) above. The appropriate alcohol, amine, or thiol may be converted completely or partially to its corresponding anion by treatment with bases, such as triethylamine, 1,8-diazabicyclo[5.4.0]undec-7-ene, K$_2$CO$_3$, NaOH, NaH, KO-t-Bu, lithium diisopropylamide or the like. The reaction is carried out in a solvent, such as DMSO, dioxane, THF, tert-butanol or DMF, at 0–200° C. for 1–24 hours.

An obtained compound of formula (I) above may be converted to another compound of formula (I) by methods well known in the art.

The chemicals used in the above-described synthetic routes may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the compounds of formula (I). When R$^1$ is a nitrogen protecting group as defined above, the subsequent N-deprotection is carried out by conventional methods. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995); and subsequent editions thereof.

The process that is described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are maleic acid, fumaric acid, succinic acid, methanesulfonic acid, acetic acid, malic acid, oxalic acid, benzoic acid, hydrochloric acid, sulphuric acid, phosphoric acid, and the like.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The necessary starting materials for preparing the compounds of formula (I) are either known or may be prepared in analogy with the preparation of known compounds.

In accordance with the present invention, the compounds of formula (I), in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of formula (I) in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavoring agents, buffers, and the like.

The compositions according to the invention can e.g. be made up in solid or liquid form for oral administration, such as tablets, pills, capsules, powders, syrups, elixirs, dispersible granules, cachets, suppositories and the like, in the form of sterile solutions, suspensions or emulsions for parenteral administration, sprays, e.g. a nasal spray, transdermal preparations, e.g. patches, and the like.

As mentioned above, the compounds of the invention may be used for the treatment of serotonin-related, especially 5-$HT_{2c}$ receptor-related disorders and conditions in a human being or an animal, such as memory disorders including Alzheimer's disease; schizophrenia; mood disorders; anxiety disorders; pain; substance abuse; sexual dysfunction; epilepsy; glaucoma; urinary incontinence; menopausal and post-menopausal hot flushes; type II diabetes; eating disorders, such as binge eating disorders, anorexia nervosa and bulimia; weight gain associated with antipsychotic drug administration; and particularly obesity.

Also within the scope of this invention is a method for modulating (e.g., inhibiting or stimulating) 5-$HT_{2c}$-receptor activity. The method includes administering to a subject in need thereof an effective amount of a compound of the formula (I).

The methods delineated herein can also include the step of identifying that a subject is in need of treatment of serotonin-related, especially 5-$HT_{2c}$ receptor-related, disorders and conditions in the subject (e.g., a mammal, a human being, a horse, a dog, or a cat).

"An effective amount" refers to an amount of a compound, which confers a therapeutic effect on the treated subject. The therapeutic effect may be objective (i.e., measurable by some test or marker) or subjective (i.e., subject gives an indication of or feels an effect). For clinical use, the compounds of the invention are formulated into pharmaceutical formulations for oral, rectal, parenteral or other mode of administration. Usually the amount of active compounds is between 0.1–95% by weight of the preparation, preferably between 0.2–20% by weight in preparations for parenteral use and preferably between 1 and 50% by weight in preparations for oral administration.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will now be illustrated with the following examples, which however, are for illustrative purposes are not intended to limit the scope of the invention.

EXAMPLES

Experimental Methods

The $^1$H-and $^{13}$C-NMR-spectra were obtained with a Bruker DPX 400. The DPFGSE-NOE experiments were obtained with a Varian INOVA 400. The mixing time was 0.8 seconds. The preparative LC was performed on a preparative LC-MS Gilson-Finnigan with a 50×20 mm S 5 μm, 120A column. The flow was 30 mL/min and different gradients of 0.1% acetic acid in water and acetonitrile were used. The accurate masses were determined with a Micromass LCT with electrospray ionization. The elemental analyses were performed with a Vario EL instrument. A Koefler bench was used to measure the melting points, which are not corrected.

Examples 1–5

Preparation of Intermediates

General Procedure for Examples 1–2

To a suspension of $LiAlH_4$ (1.2 g, 32 mmol) in dry THF (5 mL) was added the aldehyde or carboxylic acid (10 mmol) and the mixtures were stirred at room temperature for two hours. Mixtures with aldehydes as starting materials were put aside and the acids were heated at 60° C. overnight. To each mixture was added in consecutive order water (1.2 mL), 2 M aqueous NaOH (1.2 mL), and water (3.6 mL). The precipitate was filtered off and the solvent was removed under reduced pressure to yield the target products as oils.

Example 1

(5-Fluoro-2-methoxy-phenyl)-methanol

The title compound was prepared starting from 5-fluoro-2-methoxybenzaldehyde and was obtained as a light red oil (94% yield). Fragmenting MS analysis supports the stated structure. Purity 97% (GC). $^1$H NMR ($CDCl_3$) δ 3.28 (s, 3 H), 4.64 (s, 2 H), 6.78 (m, 1 H), 6.93 (m, 1 H), 7.02 (m, 1 H). $^{13}$C NMR ($CDCl_3$) δ55.73, 61.34, 110.83 (d, J=8.5 Hz), 114.22 (d, J=22.6Hz), 115.26 (d, J=23.3 Hz), 138.68 (d, J=6.4 Hz), 153.18 (d, J=2.1 Hz), 156.95 (d, J=238.8 Hz).

Example 2

(2-Phenoxymethyl-phenyl)-methanol

The title compound was prepared starting from 2-(phenoxymethyl)benzoic acid and was obtained as a light yellow oil (96% yield). Fragmenting MS analysis supports the stated structure. Purity 94% (GC). Previously reported in *J. Chem. Soc.*, 1954, 2819–2826.

Example 3

3-(S)-Methyl-1-trityl-piperazine

To a solution of 2-(S)-methylpiperazine (3.79 g, 37.9 mmol) in $CHCl_3$ (100 mL) was trityl chloride (10.56 g, 37.9 mmol) added in one portion. The exothermic reaction was stirred at ambient temperature for two hours, the organic phase was washed three times with water, dried ($MgSO_4$) and the solvent was evaporated at reduced pressure to give 12.5 g (96%) of a colorless foam that solidified to a crisp over night. $^1$H NMR ($CDCl_3$) δ 1.06 (d, J=5.5 Hz, 3 H), 1.35 (m, 1 H), 1.61 (m, 1 H), 3.01 (m, 3 H), 3.14 (m, 1 H), 3.31 (m, 1 H), 7.08 (m, 3 H), 7.16 (m, 6 H), 7.35 (m, 6 H). $^{13}$C NMR ($CDCl_3$) δ18.17, 44.46, 46.68, 51.59, 54.03, 126.26, 127.13, 127.68, 129.07 br. The racemate of the title compound is reported in *Bioorg. Med. Chem. Lett.* 2000, 10, 2643–2646.

Example 4

3-(R)-Methyl-1-trityl-piperazine

The title compound was prepared as described in WO 00/76984 starting from 2-(R)-methylpiperazine (5.51 g, 55.1 mmol). This gave 18.8 g (99%) of a white crisp. HRMS m/z calcd for $C_{24}H_{26}N_2$ (M)$^+$ 342.2096. found 342.2110.

Example 5

1-(6-Chloro-5-trifluoromethyl-pyridin-2-yl)-piperazine

Step 1: 4-(6-Chloro-5-trifluoromethyl-pyridin-2-yl)-piperazine-1-carboxylic acid tert-butyl ester To a suspension of tert-butyl-1-piperazine carboxylate (27.0 g, 145 mmol) and $K_2CO_3$ (40.0 g, 290 mmol) in DMSO (200 mL) were 2,6-dichloro-3-trifluoromethylpyridine (29.1 g, 135 mmol) and toluene (50 mL) added. The thick slurry was stirred at 80° C. for two hours, followed by addition of toluene (0.5 L) and water (1 L). The phases were separated and the organic phase was washed twice with water. The solvent from the dried ($MgSO_4$) organic phase was evaporated at reduced pressure. The solid residue was recrystallized from EtOAc/heptane to give white crystals (37 g). The filtrate from the recrystallization was concentrated and the residue chromatographed on a column of silica with hexane/EtOAc (90:10) to give further 6.0 g of product (total yield 85%). Purity 99% (HPLC); mp 125° C. Anal. ($C_{15}H_{19}ClF_3N_3O_2$) C, H, N.

Step 2: 1-(6-Chloro-5-trifluoromethyl-pyridin-2-yl)-piperazine

The title compound was prepared from the product of Step 1 above using the N-deprotection procedure given in Example 6, Step 2. This furnished 29.7 g (100%) of a light yellow oil that crystallized upon standing. A NOE between the methylene protons at C-2 in the piperazine ring and the C3-hydrogen in the pyridine ring was observed. Purity 99% (HPLC); mp 56° C. Fragmenting MS analysis supports the stated structure. HRMS m/z calcd for $C_{10}H_{11}ClF_3N_3$ (M)$^+$ 265.0594. found 265.0597. *Previously reported in EP 370560.

Example 6

1-(6-Chloro-5-trifluoromethyl-pyridin-2-yl)-3-(S)-methyl-piperazine

Step 1: 4-(6-Chloro-5-trifluoromethyl-pyridin-2-yl)-2-(S)-methyl-piperazine-1-carboxylic acid tert-butyl ester To a suspension of 2-(S)-methylpiperazine (2.65 g, 26.5 mmol) and $K_2CO_3$ (4.0 g, 29 mmol) in dry DMSO (50 mL) was slowly added 2,6-dichloro-3-trifluoromethylpyridine (5.70 g, 26.4 mmol). The reaction mixture was stirred at room temperature over night, filtered, diluted with water (ca 1 L) and extracted twice with EtOAc (100 mL). The solvent from the combined dried ($MgSO_4$) organic phases was evaporated at reduced pressure to give a yellow oil (7.4 g). This material was dissolved in MeOH (100 mL), BOC anhydride (6.0 g, 27.5 mmol) was added in one portion and the reaction mixture was stirred at room temperature for two hours. Excess BOC anhydride was quenched with pyridine (3 mL) and the mixture was left at room temperature over night. The solvent was removed at reduced pressure and the resulting oil was chromatographed on a column of silica (60×110 mm) with hexane/EtOAc (95:5, 1 L, followed by 90:10, 1 L and 80:20). Evaporation at reduced pressure of the pure fractions yielded a colorless oil (8.05 g, 80%) that solidified to a white solid over night. Purity 97% (HPLC); mp 86° C. Fragmenting MS analysis supports the stated structure. HRMS m/z calcd for $C_{16}H_{21}ClF_3N_3O_2$ (M)$^+$ 379.1274. found 379.1286.

Step 2: 1-(6-Chloro-5-trifluoromethyl-pyridin-2-yl)-3-(S)-methyl-piperazine A solution of 4-(6-chloro-5-trifluoromethyl-pyridin-2-yl)-2-(S)-methyl-piperazine-1-carboxylic acid tert-butyl ester (7.80 g, 26.4 mmol) was dissolved in $CH_2Cl_2$/TFA (50:50; 30 mL) and stirred at room temperature over night. The solvent was removed at reduced pressure and the resulting oil was taken up between alkaline water (NaOH) and $CHCl_3$. The aqueous phase was extracted once with $CHCl_3$, the combined organic phases were dried ($MgSO_4$) and the solvent was evaporated at reduced pressure to yield 5.79 g (78%) of a light yellow oil. A NOE between the methylene protons at C-2 in the piperazine ring and the C3-hydrogen in the pyridine ring was observed. Purity 100% (HPLC). Fragmenting MS analysis supports the stated structure. HRMS m/z calcd for $C_{11}H_{13}ClF_3N_3$ (M)$^+$ 279.0750. found 279.0751

Example 7

1-(6-Chloro-5-trifluoromethyl-pyridin-2-yl)-3-(R)-methylpiperazine

Step 1: 4-(6-Chloro-5-trifluoromethyl-pyridin-2-yl)-2-(R)-methyl-piperazine-1-carboxylic acid tert-butyl ester The title compound was prepared starting from 2-(R)-methylpiperazine using the procedure given in Example 6, Step 1, for the (S)-isomer and was obtained as a white crystalline solid. Yield 7.4 g (70%). Purity 99% (HPLC); mp 86° C. Fragmenting MS analysis supports the stated structure. HRMS m/z calcd for $C_{16}H_{21}ClF_3N_3O_2$ (M)$^+$ 379.1274. found 379.1269.

Step 2: 1-(6-Chloro-5-trifluoromethyl-pyridin-2-yl)-3-(R)-methylpiperazine

The title compound was prepared starting from the product of Step 1 above using the N-deprotection procedure given in Example 6, Step 2, and was obtained as a light yellow oil. Yield 4.76 g (90%). Purity 99% (HPLC). Fragmenting MS analysis supports the stated structure. HRMS m/z calcd for $C_{11}H_{13}ClF_3N_3$ (M)$^+$ 279.0750. found 279.0742.

Example 8

1-(6-Chloro-5-trifluoromethyl-pyridin-2-yl)-2-(R)-methyl-piperazine

Step 1: 1-(6-Chloro-5-trifuoromethyl-pyridin-2-yl)-2-(R)-methyl-4-trityl-piperazine A suspension of 3-(R)-methyl-1-trityl-piperazine (from Example 4; 7.80 g, 22.9 mmol), 2,6-dichloro-3-trifluoromethylpyridine (4.50 g, 20.8 mmol) and $K_2CO_3$ (4.0 g, 29 mmol) in DMSO (100 mL) was stirred at 80° C. over night. A mixture of EtOAc/toluene (50:50; 500 mL) was added to the filtered solution and the mixture were washed three times with water (1 L). The dried ($MgSO_4$) organic phase was concentrated under reduced pressure and the resulting brown oil was dissolved in heptane/EtOAc (90:10) and filtered through a plug (60×60 mm) of silica. Slow evaporation of about two thirds of the solvent at reduced pressure afforded light yellow crystals (6.11 g, 56%). Purity 100% (HPLC); mp 209° C. Fragmenting MS analysis supports the stated structure. Anal. ($C_{30}H_{27}ClF_3N_3$) C, H, N.

Step 2: 1-(6-Chloro-5-trifluoromethyl-pyridin-2-yl)-2-(R)-methyl-piperazine

A suspension of 1-(6-chloro-5-trifluoromethyl-pyridin-2-yl)-2-(R)-methyl-4-trityl-piperazine (from Step 1 above; 5.70 g, 10.9 mmol) in EtOH (70 mL) was heated to 80° C. Aqueous HCl (4 M; 6 mL) was added and the mixture was heated in an open vessel for one hour. To the clear solution was water added (100 mL) and the precipitate was filtered off. The solvent from the filtrate was evaporated down to about 10 mL, the crystals were filtered off and the evaporation continued down to 3 mL and another portion of slightly pinkish crystals were filtered off. The combined crystal fractions were taken up between alkaline water (NaOH)/$CHCl_3$. The aqueous phase was washed twice with $CHCl_3$ and the combined, dried ($MgSO_4$), organic phases were evaporated at reduced pressure to give a light yellow oil (1.75 g, 69%). A NOE between the methylene protons at C-2 in the piperazine ring and the C3-hydrogen in the pyridine ring was observed. Purity 99% (HPLC). Fragmenting MS analysis supports the stated structure. HRMS m/z calcd for $C_{11}H_{13}ClF_3N_3$ (M)$^+$ 279.0750. found 279.0744.

Example 9

1-(6-Chloro-5-trifluoromethyl-pyridin-2-yl)-2-(S)-methyl-piperazine, Hydrochloride Step 1: 1-(6-Chloro-5-trifluoromethyl-pyridin-2-yl)-2-(S)-methyl-4-trityl-piperazine The title compound was prepared starting from 3-(S)-methyl-1-trityl-piperazine (obtained in Example 3) using the procedure given in Example 8 for the (R)-isomer. Light yellow crystals; yield 5.1 g (43%). Purity 96% (HPLC); mp 210° C. Fragmenting MS analysis supports the stated structure. Anal. ($C_{30}H_{27}ClF_3N_3$) C, H, N.

Step 2: 1-(6-Chloro-5-trifluoromethyl-pyridin-2-yl)-2-(S)-methyl-piperazine, Hydrochloride The title compound was prepared starting from the product of Step 1 above using the N-detritylation procedure given in Example 8, Step 2, for the (R)-isomer. This produced 2.06 g (68%) of the free base of the title compound obtained as a pinkish oil. The free base was converted into its hydrochloride salt. Purity 99% (HPLC). Fragmenting MS analysis supports the stated structure. HRMS m/z calcd for $C_{11}H_{13}ClF_3N_3$ (M)$^+$ 279.0750. found 279.0738.

Examples 10–43

General Procedure

Volumes are expressed as total volumes.

To a 16 mm test tube was added;

0.5 mmol of the appropriate alcohol or thiol 0.4 mmol of the appropriate 6-chloro 5-trifluoromethyl-2-piperazinylpyridine in DMSO (0.5 mL)

0.65 mmol of K-t-BuO in DMSO (1.0 mL)

The reactions were stirred at room temperature for two hours followed by addition of HOAc (1.25 mmol, 75 μL). The solvent was evaporated at reduced pressure over night (Speed Vac). The remaining solids were dissolved in water/acetonitrile/HOAc, filtered, and the products were purified with preparative HPLC.

Mass detection was obtained by a Micro Mass LCP with electrospray positive ionization mode. The analytical HPLC-chromatograms were performed on a Hewlett Packard 1100 with a 50×4.6 mm Grom-SIL 100 ODS 0 AB, 3 μm column and a 50×4.6 mm YMC-AQ 5 μm column. Different gradients of 0.1% TFA in water and acetonitrile were used and the peaks were detected at 254 nm. The area % under the largest peak was reported as the purity.

Chart 1.
Starting 6-chloropyridines used in Examples 10–43.
A
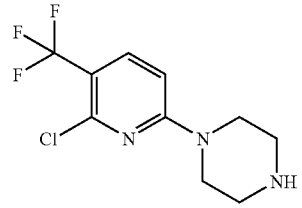
B
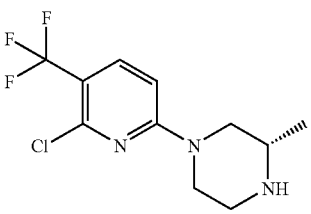
C
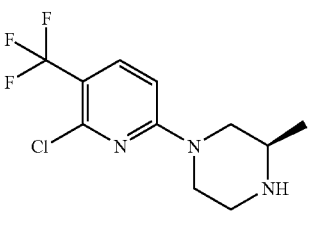
D
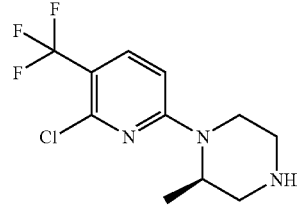
E
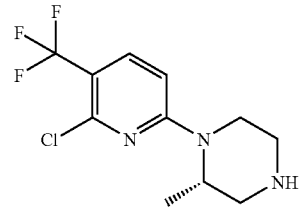
Starting alcohols and thiols used in Examples 10–43.
1
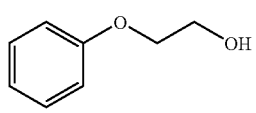
2
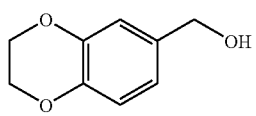
-continued
3
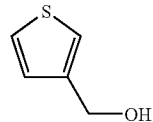
4
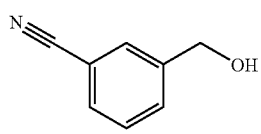
5
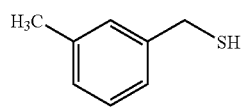
6
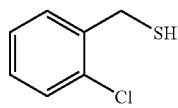
7
8
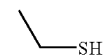
9
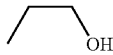
10
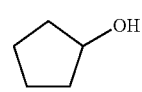
11
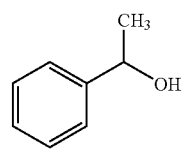
12
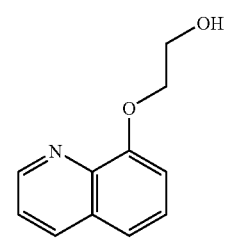
13
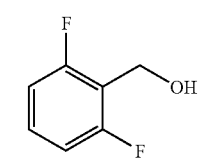

-continued

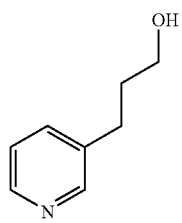

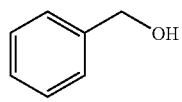

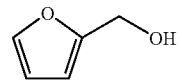

F

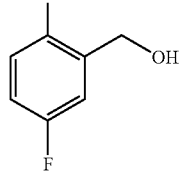

F

CH₃OH

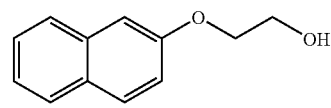

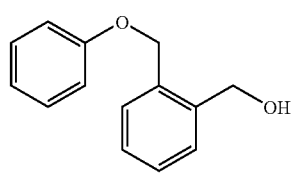

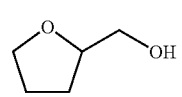

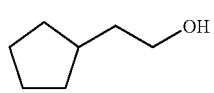

-continued

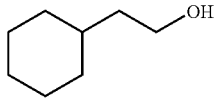

Example 10

1-[6-(2-Phenoxy-ethoxy)-5-trifluoromethyl-pyridin-2-yl]-piperazine, acetate

Starting materials A and 1, see Chart 1. Purity 99% (HPLC). MS m/z 368 (M+H)⁺. HRMS m/z calcd for $C_{18}H_{20}F_3N_3O_2$ (M)⁺ 367.1508. found 367.1508.

Example 11

1-[6-(2,3-Dihydro-benzo[1,4]dioxin-6-ylmethoxy)-5-trifluoromethyl-pyridin-2-yl]-piperazine, acetate Starting materials A and 2, see Chart 1. Purity 94% (HPLC). MS m/z 396 (M+H)⁺. HRMS m/z calcd for $C_{19}H_{20}F_3N_3O_3$ (M)⁺ 395.1457. found 395.1468.

Example 12

1-[6-(Thiophen-3-ylmethoxy)-5-trifluoromethyl-pyridin-2-yl]-piperazine, acetate

Starting materials A and 3, see Chart 1. Purity 98% (HPLC). MS m/z 344 (M+H)⁺. HRMS m/z calcd for $C_{15}H_{16}F_3N_3OS$ (M)⁺ 343.0966. found 343.0971.

Example 13

3-(6-Piperazin-1-yl-3-trifluoromethyl-pyridin-2-yloxymethyl)-benzonitrile, acetate Starting materials A and 4, see Chart 1. Purity 95% (HPLC). MS m/z 363 (M+H)⁺. HRMS m/z calcd for $C_{18}H_{17}F_3N_4O$ (M)⁺ 362.1354. found 362.1365.

Example 14

1-[6-(3-Methyl-benzylsulfanyl)-5-trifluoromethyl-pyridin-2-yl]-piperazine, acetate Starting materials A and 5, see Chart 1. Purity 96% (HPLC). MS m/z 368 (M+H)⁺. HRMS m/z calcd for $C_{18}H_{20}F_3N_3S$ (M)⁺ 367.1330. found 367.1322.

Example 15

1-[6-(2-Chloro-benzylsulfanyl)-5-trifluoromethyl-pyridin-2-yl]-piperazine, acetate Starting materials A and 6, see Chart 1. Purity 98% (HPLC). MS m/z 388 (M+H)⁺. HRMS m/z calcd for $C_{17}H_{17}ClF_3N_3S$ (M)⁺ 387.0784. found 387.0773.

Example 16

1-[6-(2,3-Difluoro-benzyloxy)-5-trifluoromethyl-pyridin-2-yl]-piperazine, acetate Starting materials A and 7, see Chart 1. Purity 100% (HPLC). MS m/z 374 (M+H)$^+$.

Example 17

1-(6-Ethylsulfanyl-5-trifluoromethyl-pyridin-2-yl)-piperazine, acetate

Starting materials A and 8, see Chart 1. Purity 96% (HPLC). MS m/z 292 (M+H)$^+$. HRMS m/z calcd for $C_{12}H_{16}F_3N_3S$ (M)$^+$ 291.1017. found 291.1018.

Example 18

1-(6-Propoxy-5-trifluoromethyl-pyridin-2-yl)-piperazine, acetate

Starting materials A and 9, see page Chart 1. Purity 100% (HPLC). MS m/z 290 (M+H)$^+$.

Example 19

1-(6-Cyclopentyloxy-5-trifluoromethyl-pyridin-2-yl)-piperazine, acetate

Starting materials A and 10, see Chart 1. Purity 100% (HPLC). MS m/z 316 (M+H)$^+$. HRMS m/z calcd for $C_{15}H_{20}F_3N_3O$ (M)$^+$ 315.1558. found 315.1551.

Example 20

1-[6-(1-Phenyl-ethoxy)-5-trifluoromethyl-pyridin-2-yl]-piperazine, acetate

Starting materials A and 11, see Chart 1. Purity 100% (HPLC). MS m/z 352 (M+H)$^+$. HRMS m/z calcd for $C_{18}H_{20}F_3N_3O$ (M)$^+$ 351.1558. found 351.1573.

Example 21

8-[2-(6-Piperazin-1-yl-3-trifluoromethyl-pyridin-2-yloxy)-ethoxyl-quinoline, acetate Starting material A and 12*, see page Chart 1. Purity 98% (HPLC). MS m/z 419 (M+H)$^+$. HRMS m/z calcd for $C_{21}H_{21}F_3N_4O_2$ (M)$^+$ 418.1617. found 418.1625.
*Starting material 12 was prepared as described in WO 00/76984.

Example 22

1-[6-(2,6-Difluoro-benzyloxy)-5-trifluoromethyl-pyridin-2-yl]-piperazine, acetate Starting material A and 13, see Chart 1. Purity 96% (HPLC). MS m/z 374 (M+H)$^+$. HRMS m/z calcd for $C_{17}H_{16}F_5N_3O$ (M)$^+$ 373.1214. found 373.1209.

Example 23

1-[6-(3-{Pyridin-3-yl}propoxy)-5-trifluoromethyl-pyridin-2-yl]-piperazine, acetate Starting material A and 14, see Chart 1. Purity 99% (HPLC). MS m/z 367 (M+H)$^+$. HRMS m/z calcd for $C_{18}H_{21}F_3N_4O$ (M)$^+$ 366.1667. found 366.1677.

Example 24

1-(6-Benzyloxy-5-trifluoromethyl-pyridin-2-yl)-piperazine, acetate

Starting material A and 15, see Chart 1. Purity 99% (HPLC). MS m/z 338 (M+H)$^+$. HRMS m/z calcd for $C_{17}H_{18}F_3N_3O$ (M)$^+$ 337.1402. found 337.1408.

Example 25

1-[6-(Furan-2-ylmethoxy)-5-trifluoromethyl-pyridin-2-yl]-piperazine, acetate

Starting material A and 16, see Chart 1. Purity 96% (HPLC). MS m/z 328 (M+H)$^+$. HRMS m/z calcd for $C_{15}H_{16}F_3N_3O_2$ (M)$^+$ 327.1195. found 327.1195.

Example 26

1-{6-2-(2,6-Difluoro-phenoxy)-ethoxy]-5-trifluoromethyl-pyridin-2-yl}-piperazine, acetate Starting materials A and 17*, see Chart 1. Purity 98% (HPLC). MS m/z 404 (M+H)$^+$. HRMS m/z calcd for $C_{18}H_{18}F_5N_3O_2$ (M)$^+$ 403.1319. found 403.1326.
*Starting material 17 was prepared from 2,6-diflurophenol and ethylene carbonate according to the general procedure described in WO 00/76984 (Example 91). MS analysis supported the stated structure. HRMS m/z calcd for $C_8H_8F_2O_2$ (M)$^+$ 174.0492, found 174.0491.

Example 27

1-[6-(2-Chloro-benzylsulfanyl)-5-trifluoromethyl-pyridin-2-yl]-2-(R)-methyl-piperazine, acetate Starting materials D and 6, see Chart 1. Purity 96% (HPLC). MS m/z 402 (M+H)$^+$. HRMS m/z calcd for $C_{18}H_{19}ClF_3N_3S$ (M)$^+$ 401.0940. found 401.0926.

Example 28

1-(6-Ethylsulfanyl-5-trifluoromethyl-pyridin-2-yl)-3-(S)-methyl-piperazine, acetate Starting materials B and 8, see Chart 1. Purity 100% (HPLC). MS m/z 306 (M+H)$^+$. HRMS m/z calcd for $C_{13}H_{18}F_3N_3S$ (M)$^+$ 305.1174. found 305.1163.

Example 29

1-(6-Ethylsulfanyl-5-trifuoromethyl-pyridin-2-yl)-3-(R)-methyl-piperazine, acetate Starting materials C and 8, see Chart 1. Purity 95% (HPLC). MS m/z 306 (M+H)$^+$. HRMS m/z calcd for $C_{13}H_{18}F_3N_3S$ (M)$^+$ 305.1174. found 305.1168.

Example 30

1-(6-Ethylsulfanyl-5-trifluoromethyl-pyridin-2-yl)-2-(R)-methyl-piperazine, acetate Starting materials D and 8, see Chart 1. Purity 100% (HPLC). MS m/z 306 (M+H)$^+$.
HRMS m/z calcd for $C_{13}H_{18}F_3N_3S$ (M)$^+$ 305.1174. found 305.1160.

Example 31

1-(6-Benzyloxy-5-trifluoromethyl-pyridin-2-yl)-3-(S)-methyl-piperazine, acetate

Starting materials B and 15, see Chart 1. Purity 100% (HPLC). MS m/z 352 (M+H)$^+$. HRMS m/z calcd for $C_{18}H_{20}F_3N_3O$ (M)$^+$ 351.1558. found 351.1553.

Example 32

1-(6-Benzyloxy-5-trifluoromethyl-pyridin-2-yl)-3-(R)-methyl-piperazine, acetate

Starting materials C and 15, see Chart 1. Purity 99% (HPLC). MS m/z 352 (M+H)$^+$. HRMS m/z calcd for $C_{18}H_{20}F_3N_3O$ (M)$^+$ 351.1558. found 351.1541.

Example 33

1-(6-Benzyloxy-5-trifluoromethyl-pyridin-2-yl)-2-(R)-methyl-piperazine, acetate

Starting materials D and 15, see Chart 1. Purity 99% (HPLC). MS m/z 352 (M+H)$^+$. HRMS m/z calcd for $C_{18}H_{20}F_3N_3O$ (M)$^+$ 351.1558. found 351.1551.

Example 34

1-(6-Benzyloxy-5-trifluoromethyl-pyridin-2-yl)-2-(S)-methyl-piperazine, acetate

Starting materials E and 15, see Chart 1. Purity 100% (HPLC). MS m/z 352 (M+H)$^+$. HRMS m/z calcd for $C_{18}H_{20}F_3N_3O$ (M)$^+$ 351.1558. found 351.1552.

Example 35

1-(6-Methoxy-5-trifluoromethyl-pyridin-2-yl)-piperazine, acetate

Starting materials A and 18, see Chart 1. Purity 100% (HPLC). MS m/z 262 (M+H)$^+$. HRMS m/z calcd for $C_{11}H_{14}F_3N_3O$ (M)$^+$ 261.1089. found 261.1100.

Example 36

1-[6-(5-Fluoro-2-methoxy-benzyloxy)-5-trifluoromethyl-pyridin-2-yl]-piperazine, acetate Starting materials A and 19, see Chart 1. Purity 96% (HPLC). MS m/z 386 (M+H)$^+$. HRMS m/z calcd for $C_{18}H_{19}F_4N_3O_2$ (M)$^+$ 385.1413. found 385.1408.

Example 37

1-{6-[2-(Naphthalen-2-yloxy)-ethoxyl]-5-trifluoromethyl-pyridin-2-yl}-piperazine, acetate Starting materials A and 20, see Chart 1. Purity 100% (HPLC). MS m/z 418 (M+H)$^+$. HRMS m/z calcd for $C_{22}H_{22}F_3N_3O_2$ (M)$^+$ 417.1664. found 417.1658.

Example 38

1-[6-(2-Chloro-benzylsulfanyl)-5-trifluoromethyl-pyridin-2-yl]-3-(S)-methyl-piperazine, acetate Starting materials B and 6, see Chart 1. Purity 100% (HPLC). MS m/z 402 (M+H)$^+$. HRMS m/z calcd for $C_{18}H_{19}ClF_3N_3S$ (M)$^+$ 401.0940. found 401.0950.

Example 39

1-[6-(2-Chloro-benzylsulfanyl)-5-trifluoromethyl-pyridin-2-yl]-2-(S)-methyl-piperazine, acetate Starting materials E and 6, see Chart 1. Purity 99% (HPLC). MS m/z 402 (M+H)$^+$. HRMS m/z calcd for $C_{18}H_{19}F_3N_3S$ (M)$^+$ 401.0940. found 401.0942.

Example 40

1-[6-(2-Phenoxymethyl-benzyloxy)-5-trifluoromethyl-pyridin-2-yl]-piperazine, acetate Starting materials A and 21, see Chart 1. Purity 100% (HPLC). MS m/z 444 (M+H)$^+$. HRMS m/z calcd for $C_{24}H_{24}F_3N_3O_2$ (M)$^+$ 443.1821. found 443.1841.

Example 41

1-[6-Tetrahydro-furan-2-ylmethoxy)-5-trifluoromethyl-pyridin-2-yl]-piperazine, acetate Starting materials A and 22, see Chart 1. Purity 97% (HPLC). MS m/z 332 (M+H)$^+$. HRMS m/z calcd for $C_{15}H_{20}F_3N_3O_2$ (M)$^+$ 331.1508. found 331.1504.

Example 42

1-[6-(2-Cyclopentyl-ethoxy)-5-trifluoromethyl-pyridin-2-yl]-piperazine, acetate

Starting materials A and 23, see Chart 1. Purity 100% (HPLC). MS m/z 344 (M+H)$^+$.

Example 43

1-[6-(2-Cyclohexyl-ethoxy)-5-trifluoromethyl-pyridin-2-yl]-piperazine, acetate

Starting materials A and 24, see Chart 1. Purity 90% (HPLC). MS m/z 358 (M+H)$^+$. HRMS m/z calcd for $C_{18}H_{26}F_3N_3O$ (M)$^+$ 357.2028. found 357.2040.

Preparation of a Pharmaceutical Composition

Example

Preparation of Tablets

|   | Ingredients | mg/tablet |
|---|---|---|
| 1. | Active compound of formula (I) | 10.0 |
| 2. | Cellulose, microcrystalline | 57.0 |
| 3. | Calcium hydrogen phosphate | 15.0 |
| 4. | Sodium starch glycolate | 5.0 |
| 5. | Silicon dioxide, colloidal | 0.25 |
| 6. | Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

Pharmacological Methods

The ability of a compound of the invention to bind or act at specific 5-HT receptor subtypes can be determined using in vitro and in vivo assays known in the art. The biological activity of compounds prepared in the Examples was tested using different tests.

Affinity Assay

The 5-HT$_{2c}$ receptor affinity of compounds in the Examples was determined in competition experiments, where the ability of each compound in serial dilution to displace $^3$H-labelledlabeled 5-HT, bound to membranes prepared from a transfected HEK293 cell line stably expressing the human 5-HT$_{2c}$ receptor protein, was monitored by Scintillation Proximity Assay technology. Non-specific binding was defined using 5 μM mianserin. Results obtained for exemplary compounds of the invention are illustrated in Table 1 below. The 5-HT$_{2c}$ receptor affinity values, expressed as percent inhibition of binding of the radioligand at 50 nM of test compound, were in the range of 10%–95%. The $K_i$ values for the compounds towards the 5-HT$_{2c}$ receptor were in the range 0.5–5000 nM.

TABLE 1

5-HT$_{2c}$ receptor Affinity

| Compound | $K_i$ (nM) |
|---|---|
| Example 15 | 1 |
| Example 17 | 15 |
| Example 21 | 246 |
| Example 25 | 14 |
| Example 30 | 24 |
| Example 36 | 5 |
| Example 38 | 6 |

Efficacy Assay

The agonist efficacy at the 5-HT$_{2c}$ receptor of the compounds in the Examples was determined by the ability of each compound to mobilise intracellular calcium in transfected HEK293 cells, stably expressing the human 5-HT$_{2c}$ receptor protein, using the calcium-chelating fluorescent dye FLUO-3 (Sigma, St. Louis, Mo., U.S.A.).

The maximum responses of the compounds in the Examples were in the range of 0–102% relative to the maximum response of 5-HT (serotonin) at a concentration of 1 μM.

The invention claimed is:

1. A compound of the formula (I):

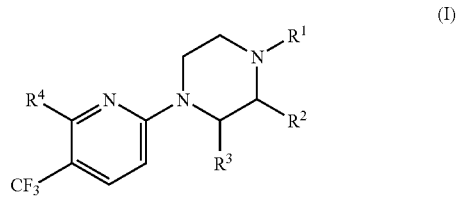

wherein
R$^1$ is selected from H, C$_{1-4}$ alkyl, 2-hydroxyethyl, 2-cyanoethyl, and tetrahydropyran-2-yl;
R$^2$ and R$^3$ each, independently, represent H or CH$_3$;
R$^4$ is selected from O—R$^5$, NH—R$^5$ or S—R$^5$, wherein R$^5$ is selected from aryl, aryl-C$_{1-6}$-alkyl, aryloxy-C$_{2-6}$-alkyl, heteroaryl, heteroaryl-C$_{1-6}$-alkyl, heteroaryloxy-C$_{2-6}$-alkyl, C$_{3-6}$-cycloalkyl, C$_{3-6}$-cycloalkyl-C$_{1-4}$-alkyl, C$_{1-6}$-alkyl, 2-tetrahydrofuryl, 3-tetrahydrofuryl, 2-tetrahydrofurfuryl, 3-tetrahydrofurfuryl, piperidine-4-yl, tetrahydropyran-4-yl, C$_{3-6}$-alkynyl, C$_{3-6}$-alkenyl, or fluoro-C$_{2-4}$-alkyl;
and wherein any aryl or heteroaryl residue, alone or as part of another group, may be unsubstituted or substituted with one or more of C$_{1-4}$-alkyl, C$_{1-4}$-alkoxy, C$_{1-4}$-alkylthio, C$_{2-4}$-acyl, C$_{1-4}$-alkylsulphonyl, cyano, nitro, hydroxy, C$_{2-6}$-alkenyl, C$_{2-6}$-alkynyl, fluoromethyl, trifluoromethyl, trifluoromethoxy, halogen, —N(R$^6$)(R$^7$), aryl, aryloxy, arylthio, aryl-C$_{1-4}$-alkyl, aryl-C$_{2-4}$-alkenyl, aryl-C$_{2-4}$-alkynyl, heteroaryl, heteroaryloxy, heteroarylthio, heteroaryl-C$_{1-4}$-alkyl, aryl-C$_{1-4}$-alkoxy, aryloxy-C$_{1-4}$-alkyl, or dimethylamino-C$_{2-4}$-alkoxy, wherein
R$^6$ and R$^7$ are, independently of each other, hydrogen, methyl or ethyl; or form a pyrrolidine, piperazine, morpholine, thiomorpholine or a piperidine ring together with the nitrogen atom to which they are bound;
and wherein any aryl or heteroaryl residue as substituents on aryl or heteroaryl, alone or as part of another group, in turn may be substituted in one or more positions independently of each other by C$_{1-4}$-alkyl, C$_{1-4}$-alkoxy, halogen, trifluoromethyl, cyano, hydroxy or dimethylamino;
and pharmaceutically acceptable salts, hydrates, geometrical isomers, tautomers, optical isomers, and N-oxides thereof.

2. The compound of claim 1, wherein R$^1$ is hydrogen.

3. The compound of claim 1, wherein R$^4$ is selected from O—R$^5$ and S—R$^5$.

4. The compound of claim 3, wherein R$^5$ is selected from aryl-C$_{1-6}$-alkyl, aryloxy-C$_{2-6}$-alkyl, heteroaryl-C$_{1-6}$-alkyl, heteroaryloxy-C$_{2-6}$-alkyl, C$_{3-6}$-cycloalkyl, C$_{3-6}$-cycloalkyl-C$_{1-4}$-alkyl, C$_{1-6}$-alkyl, 2-tetrahydrofurfuryl, and wherein any aryl or heteroaryl residue, alone or as part of another group, may be unsubstituted or substituted with one or more of C$_{1-4}$-alkyl, C$_{1-4}$-alkoxy, cyano, halogen, or aryloxy-C$_{1-4}$-alkyl.

5. The compound of claim 4, wherein R$^5$ is selected from benzyl, 2-chlorobenzyl, 3-cyanobenzyl, 2-cyclohexylethyl, cyclopentyl, 2-cyclopentylethyl, 2,3-difluorobenzyl, 2,6-difluorobenzyl, 2-(2,6-difluorophenoxy)ethyl, 2,3-dihydrobenzo[1,4]dioxin-6-ylmethyl, ethyl, 5-fluoro-2-methoxybenzyl, furan-2-ylmethyl, methyl, α-methylbenzyl, 3-methylbenzyl, 2-(naphthalene-2-yloxy)ethyl, 2-phenoxyethyl, 2-phenoxymethylbenzyl, n-propyl, 3-(pyridin-3-yl)-n-propyl, 2-(8-quinolinyloxy)ethyl, tetrahydrofuran-2-ylmethyl, or 3-thienylmethyl.

6. The compound of claim 1, wherein the carbon atom, to which $R^2$ is attached, has the (S)-configuration when $R^2$ is methyl and $R^1$ and $R^3$ both are hydrogen.

7. The compound of claim 1, wherein the carbon atom, to which $R^3$ is attached, has the (R)-configuration when $R^3$ is methyl and $R^1$ and $R^2$ both are hydrogen.

8. The compound of claim 1, wherein the compound is:
1-[6-(2-Phenoxy-ethoxy)-5-trifluoromethyl-pyridin-2-yl]-piperazine, acetate;
1-[6-(2,3-Dihydro-benzo[1,4]dioxin-6-ylmethoxy)-5-trifluoromethyl-pyridin-2-yl]-piperazine, acetate;
1-[6-(Thiophen-3-ylmethoxy)-5-trifluoromethyl-pyridin-2-yl]-piperazine, acetate;
3-(6-Piperazin-1-yl-3-trifluoromethyl-pyridin-2-yloxymethyl)-benzonitrile, acetate;
1-[6-(3-Methyl-benzylsulfanyl)-5-trifluoromethyl-pyridin-2-yl]-piperazine, acetate;
1-[6-(2-Chloro-benzylsulfanyl)-5-trifluoromethyl-pyridin-2-yl]-piperazine, acetate;
1-[6-(2,3-Difluoro-benzyloxy)-5-trifluoromethyl-pyridin-2-yl]-piperazine, acetate;
1-(6-Ethylsulfanyl-5-trifluoromethyl-pyridin-2-yl)-piperazine, acetate;
1-(6-Propoxy-5-trifluoromethyl-pyridin-2-yl)-piperazine, acetate;
1-(6-Cyclopentyloxy-5-trifluoromethyl-pyridin-2-yl)-piperazine, acetate;
1-[6-(1-Phenyl-ethoxy)-5-trifluoromethyl-pyridin-2-yl]-piperazine, acetate;
8-[2-(6-Piperazin-1-yl-3-trifluoromethyl-pyridin-2-yloxy)-ethoxy]-quinoline, acetate;
1-[6-(2,6-Difluoro-benzyloxy)-5-trifluoromethyl-pyridin-2-yl]-piperazine, acetate;
1-[6-(3-{Pyridin-3-yl}propoxy)-5-trifluoromethyl-pyridin-2-yl]-piperazine, acetate;
1-(6-Benzyloxy-5-trifluoromethyl-pyridin-2-yl)-piperazine, acetate;
1-[6-(Furan-2-ylmethoxy)-5-trifluoromethyl-pyridin-2-yl]-piperazine, acetate;
1-{6-[2-(2,6-Difluoro-phenoxy)-ethoxy]-5-trifluoromethyl-pyridin-2-yl}-piperazine, acetate;
1-[6-(2-Chloro-benzylsulfanyl)-5-trifluoromethyl-pyridin-2-yl]-2-(R)-methyl-piperazine, acetate;
1-(6-Ethylsulfanyl-5-trifluoromethyl-pyridin-2-yl)-3-(S)-methyl-piperazine, acetate;
1-(6-Ethylsulfanyl-5-trifluoromethyl-pyridin-2-yl)-3-(R)-methyl-piperazine, acetate;
1-(6-Ethylsulfanyl-5-trifluoromethyl-pyridin-2-yl)-2-(R)-methyl-piperazine, acetate;
1-(6-Benzyloxy-5-trifluoromethyl-pyridin-2-yl)-3-(S)-methyl-piperazine, acetate;
1-(6-Benzyloxy-5-trifluoromethyl-pyridin-2-yl)-3-(R)-methyl-piperazine, acetate;
1-(6-Benzyloxy-5-trifluoromethyl-pyridin-2-yl)-2-(R)-methyl-piperazine, acetate;
1-(6-Benzyloxy-5-trifluoromethyl-pyridin-2-yl)-2-(S)-methyl-piperazine, acetate;
1-(6-Methoxy-5-trifluoromethyl-pyridin-2-yl)-piperazine, acetate;
1-[6-(5-Fluoro-2-methoxy-benzyloxy)-5-trifluoromethyl-pyridin-2-yl]-piperazine, acetate;
1-{6-[2-(Naphthalen-2-yloxy)-ethoxy]-5-trifluoromethyl-pyridin-2-yl}-piperazine, acetate;
1-[6-(2-Chloro-benzylsulfanyl)-5-trifluoromethyl-pyridin-2-yl]-3-(S)-methyl-piperazine, acetate;
1-[6-(2-Chloro-benzylsulfanyl)-5-trifluoromethyl-pyridin-2-yl]-2-(S)-methyl-piperazine, acetate;
1-[6-(2-Phenoxymethyl-benzyloxy)-5-trifluoromethyl-pyridin-2-yl]-piperazine, acetate;
1-[6-Tetrahydro-furan-2-ylmethoxy)-5-trifluoromethyl-pyridin-2-yl]-piperazine, acetate;
1-[6-(2-Cyclopentyl-ethoxy)-5-trifluoromethyl-pyridin-2-yl]-piperazine, acetate; or
1-[6-(2-Cyclohexyl-ethoxy)-5-trifluoromethyl-pyridin-2-yl]-piperazine, acetate.

9. A pharmaceutical composition comprising a compound of formula (I) of claim 1 and a pharmaceutically acceptable carrier.

10. A method for the treatment of a disorder or condition selected from anxiety disorders; epilepsy; urinary incontinence; and menopausal and post-menopausal hot flushes in a subject in need thereof, the method comprising administering to the subject an effective amount of a compound of formula (I) of claim 1.

11. A method for the treatment of obesity in a subject in need thereof, the method comprising administering to the subject an effective amount of a compound of formula (I) of claim 1.

12. The method of claim 10, wherein the subject is a human.

13. The method of claim 10, wherein the subject is an animal.

14. The method of claim 11, wherein the subject is an animal.

15. The method of claim 11, wherein the subject is a human.

16. A method for preparing a pharmaceutical composition, the method comprising combining a compound of formula (I) of claim 1 with a pharmaceutically acceptable carrier.

17. A method of making a compound of formula (I) of claim 1, by reacting a compound of the following formula (II):

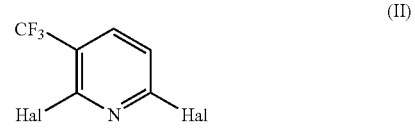

wherein Hal is halogen;
with an appropriate piperazine derivative of formula (III):

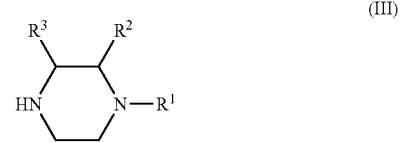

wherein
$R^1$ is H or $C_{1-4}$ alkyl, 2-hydroxyethyl, 2-cyanoethyl, or tetrahydropyran-2-yl; and $R^2$ and $R^3$ each, independently, represent H or $CH_3$;
to produce a compound of formula (IV)

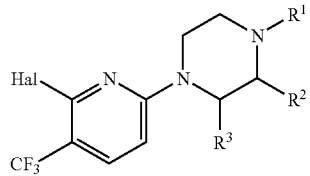

(IV)

wherein
$R^1$, $R^2$ and $R^3$ have meaning as in formula (III); and
Hal is halogen;
and reacting the compound of formula (IV) with an appropriate alcohol, amine or thiol, as defined by O—$R^5$, NH—$R^5$ or S—$R^5$, or its corresponding anions, thereby making a compound of formula (I) of claim 1.

18. The method of claim 10, wherein the disorder or condition is selected from urinary incontinence.

19. The method of claim 10, wherein the disorder or condition is selected from menopausal and post-menopausal hot flushes.

* * * * *